(12) United States Patent
Sakaguchi et al.

(10) Patent No.: US 9,186,279 B2
(45) Date of Patent: Nov. 17, 2015

(54) DISPOSABLE DIAPER

(75) Inventors: Satoru Sakaguchi, Kagawa (JP); Tomomi Oku, Kagawa (JP); Hideki Matsushima, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 669 days.

(21) Appl. No.: 13/498,952

(22) PCT Filed: Oct. 1, 2010

(86) PCT No.: PCT/JP2010/005925
§ 371 (c)(1),
(2), (4) Date: Jun. 6, 2012

(87) PCT Pub. No.: WO2011/040046
PCT Pub. Date: Apr. 7, 2011

(65) Prior Publication Data
US 2012/0245549 A1    Sep. 27, 2012

(30) Foreign Application Priority Data

Oct. 1, 2009    (JP) ................. 2009-230041

(51) Int. Cl.
*A61F 13/56* (2006.01)
*A61F 13/15* (2006.01)
*A61F 13/49* (2006.01)

(52) U.S. Cl.
CPC ..... *A61F 13/15585* (2013.01); *A61F 13/15756* (2013.01); *A61F 13/49014* (2013.01); *A61F 13/49017* (2013.01); *A61F 13/5622* (2013.01)

(58) Field of Classification Search
CPC ............... A61F 13/49061; A61F 2013/49095; A61F 13/49453; A61F 13/51484; A61F 13/5148; A61F 2013/49092; A61F 13/49014; A61F 13/4906; A61F 2013/49063
USPC ........................... 604/385.04, 385.25
See application file for complete search history.

(56) References Cited

U.S. PATENT DOCUMENTS 6,132,411 A    10/2000 Huber et al.
6,632,213 B1 * 10/2003 Lehman et al. .......... 604/385.25
(Continued)

FOREIGN PATENT DOCUMENTS

CN    101222891 A    7/2008
EP    1402867 A2    3/2004
(Continued)

OTHER PUBLICATIONS

International Search Report for PCT/JP2010/005925 mailed Jan. 11, 2011.
(Continued)

*Primary Examiner* — Lynne Anderson
*Assistant Examiner* — Peter S Vasat
(74) *Attorney, Agent, or Firm* — Hauptman Ham, LLP (57) ABSTRACT

A disposable diaper includes: a main body having a liquid-permeable topsheet, a liquid-impermeable outer sheet an absorber provided between the topsheet and the outer sheet, and a gather. The gather includes a plurality of elastic members arranged in a width direction outboard of the absorber. The elastic members are fixed to the gather in a state where the elastic members are stretched in a longitudinal direction. A side flap is located in one of end portions of the main body in the longitudinal direction and projects outwardly beyond at least one of end portions of the main body in the width direction. A joint portion joins the side flap and the main body. In a spread-out state of the disposable diaper, an outermost elastic member among the elastic members is arranged outboard of the joint portion in the width direction.

20 Claims, 9 Drawing Sheets

(56) References Cited

U.S. PATENT DOCUMENTS

| | | |
|---|---|---|
| 2003/0088230 A1* | 5/2003 | Balogh et al. .......... 604/385.101 |
| 2004/0073188 A1 | 4/2004 | Mitsui et al. |
| 2004/0082931 A1 | 4/2004 | Tani |
| 2007/0073260 A1 | 3/2007 | Roe |
| 2008/0312631 A1 | 12/2008 | Okuda |

FOREIGN PATENT DOCUMENTS

| | | |
|---|---|---|
| EP | 1413277 A1 | 4/2004 |
| EP | 1902694 A1 | 3/2008 |
| JP | 2000513636 A | 10/2000 |
| JP | 2004129878 A | 4/2004 |
| JP | 2004174210 A | 6/2004 |
| JP | 2007020658 A | 2/2007 |
| JP | 2009509619 A | 3/2009 |
| TW | 200412914 A | 8/2004 |
| WO | 2011040042 A1 | 4/2011 |

OTHER PUBLICATIONS

Office Action issued Jun. 22, 2014, corresponds to Egyptian patent application No. 584/2012.

Office Action mailed on Jul. 2, 2013 corresponds to Japanese Patent Application No. 2009-230041.

Extended European Search Report dated Oct. 2, 2013, corresponds to European patent application No. 10820167.4.

Office Action issued Dec. 18, 2014, corresponding to Australian patent application No. 2010302090.

Office Action issued Mar. 14, 2015, corresponding to Egyptian patent application No. 584/2012.

Office Action issued May 22, 2015, corresponding to Taiwanese patent application No. 099133529.

* cited by examiner

DISPOSABLE DIAPER

RELATED APPLICATIONS

The present application is a national phase of PCT/2010/005925 filed on Oct. 1, 2010 and is based on, and claims priority from, Japanese Application Number 2009-230041, filed Oct. 1, 2009.

TECHNICAL FIELD

The present disclosure relates to a disposable diaper.

BACKGROUND ART

A known open-type diaper includes a waistline member and a main body. The open-type diaper also includes fastening tapes to join the waistline member and the main body, and leakage prevention portions configured to prevent body discharge from leaking between the main body and the wearer's legs as disclosed, for example, in Published Japanese Translation of PCT International Application No. 2000-513636. Thereby, it is possible to fit the open-type diaper on the waistline of the wearer and to bring the diaper into close contact with the crotch of the wearer.

When the known disposable diaper is put on the wearer, an absorbent surface of the main body is firstly fitted to the crotch of the wearer. Subsequently, the waistline member is stretched so as to fit to the waistline of the wearer, and is then fastened to the main body with the fastening tapes.

SUMMARY OF INVENTION

In an aspect, a disposable diaper includes: a main body having a liquid-permeable topsheet, a liquid-impermeable outer sheet an absorber provided between the topsheet and the outer sheet, and a gather. The main body has a longitudinal direction and a width direction orthogonal to the longitudinal direction. The gather includes a plurality of elastic members arranged in the width direction outboard of the absorber. The elastic members are fixed to the gather in a state where the elastic members are stretched in the longitudinal direction. A side flap is located in one of end portions of the main body in the longitudinal direction and projects outwardly beyond at least one of end portions of the main body in the width direction. A joint portion joins the side flap and the main body. In a spread-out state of the disposable diaper, an outermost elastic member among the elastic members is arranged outboard of the joint portion in the width direction.

DESCRIPTION OF EMBODIMENTS

The following is the inventors' observation regarding the known disposable diaper.

The known diaper is provided with side panels to define the waistline member. Joint portions between the side panels and the main body are respectively provided outboard of the leakage prevention portions in the width direction of the main body. Thus, when the side panels are stretched so as to fit to the waistline of the wearer, a force is applied to the main body most strongly at the joint portions outboard of the leakage prevention portions.

Provided with a long and narrow elastic member which is stretchable in a longitudinal direction, each of the leakage prevention portions is less likely to be pulled outward from the main body in the width direction. Accordingly, when the side panels are stretched so as to fit to the waistline of the wearer, the leakage prevention portion located inboard of a base point (the joint portion) of a pulling force is not extended largely, because the base point of the pulling force is located outboard of the leakage prevention portion.

For this reason, when the disposable diaper is worn by the wearer, the leakage prevention portion is not fully extended in the width direction. Consequently, the disposable diaper may be worn with a part of the absorbent surface being covered by the leakage prevention portion. This causes the area of absorption to be reduced, leading to lower absorbency and/or side leakage.

Disposable diapers according to exemplary embodiments of the present invention will be now described with reference to the drawings. Note that, in the following description of the drawings, same or similar reference signs denote same or similar elements and portions. In addition, it should be noted that the drawings are schematic and are not to scale unless otherwise specified. Moreover, the drawings do not necessarily reflect the real life dimensional relationships and ratios of components.

Disposable Diaper

Figure 1:
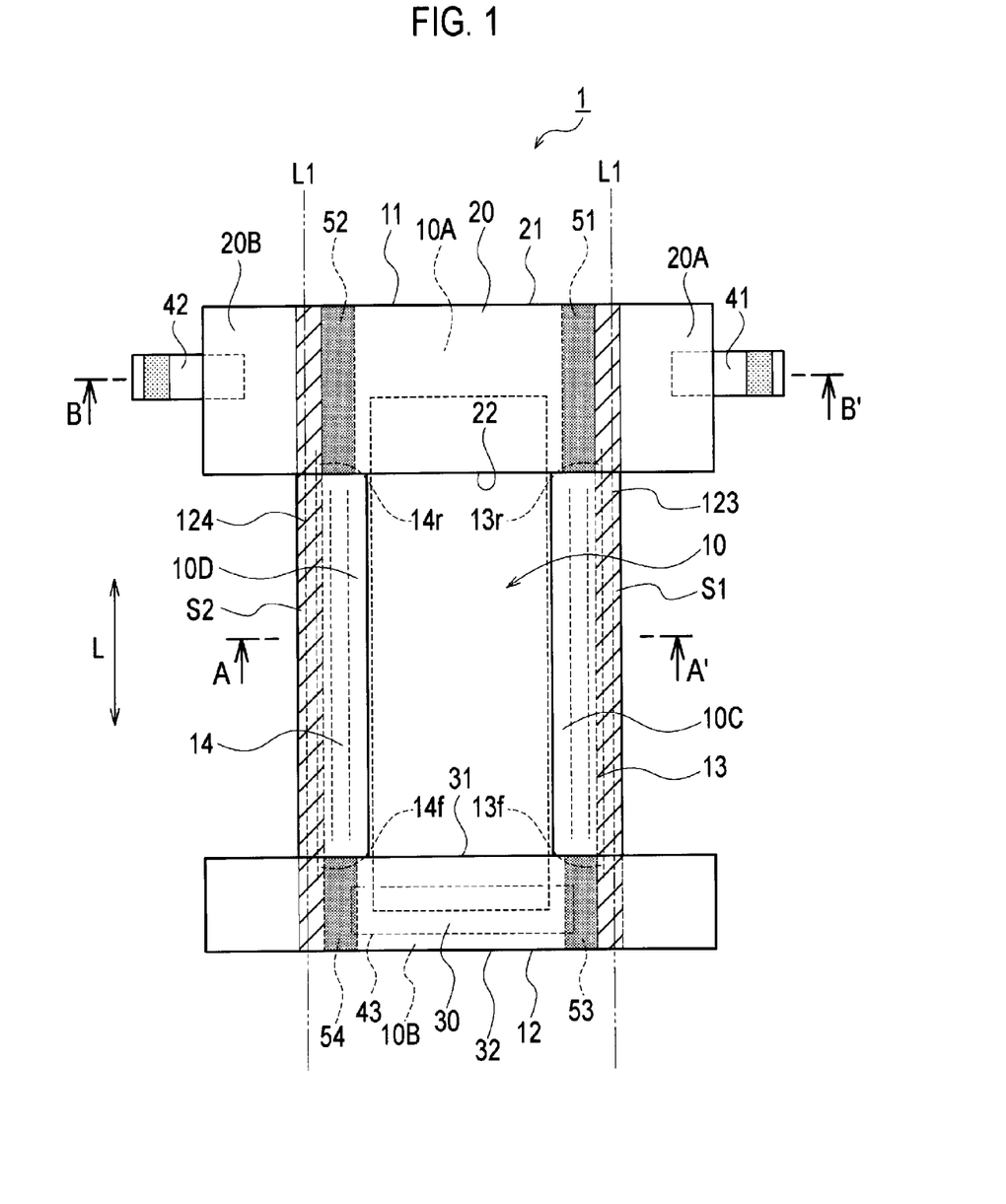
FIG. 1 is a plan view of a disposable diaper according to an embodiment of the present invention.
Figure 2:
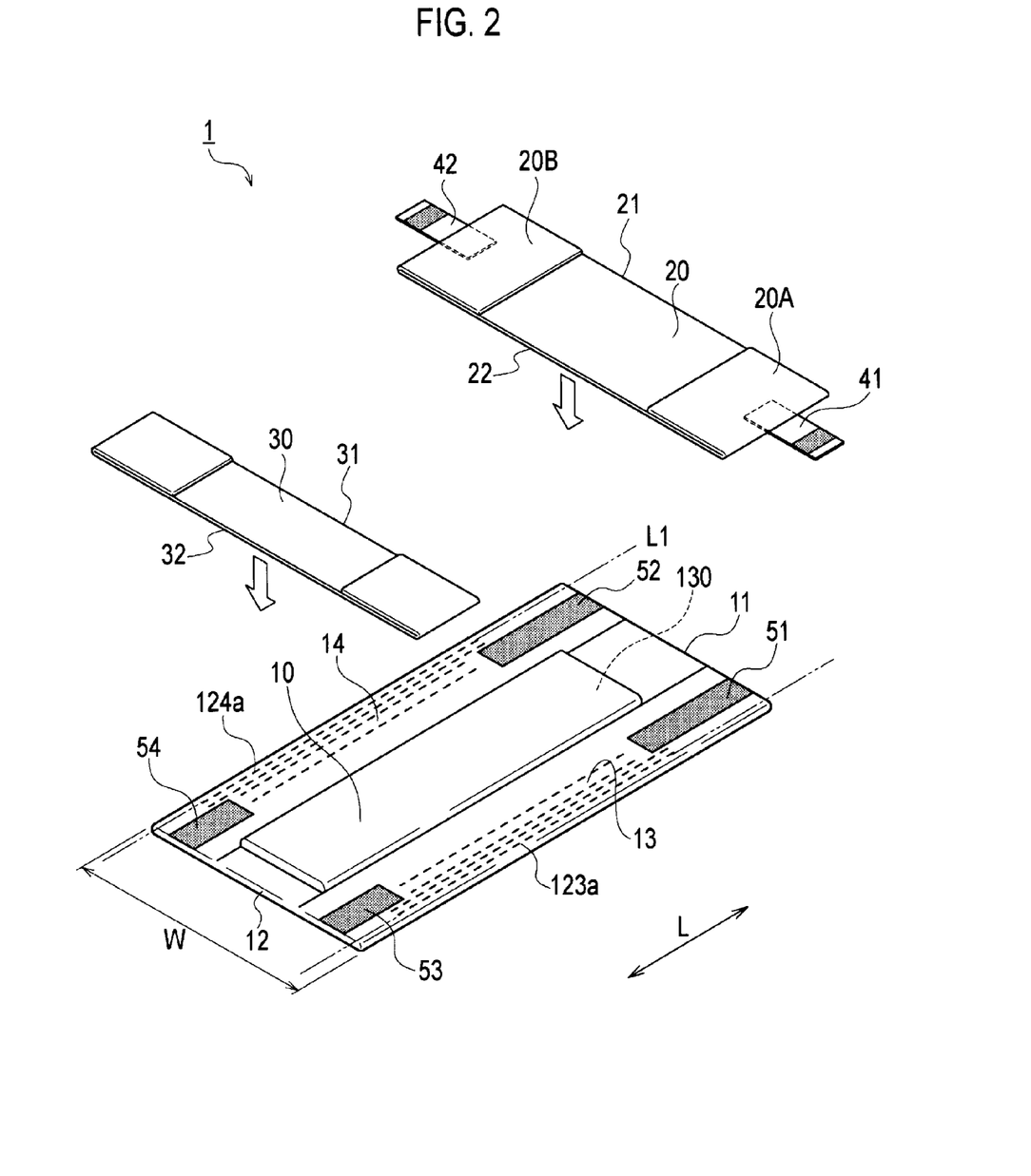
FIG. 2 is an exploded perspective view of the disposable diaper.

FIG. 1 is a plan view of a disposable diaper 1 according to an embodiment of the present invention. FIG. 2 is an exploded perspective view of the disposable diaper 1. The disposable diaper 1 is an open-type diaper and includes a main body 10, a back side flap 20 and a belly side flap 30. The back side flap 20 of the disposal diaper 1 is fitted to the back of the waistline of a wearer, while the belly side flap 30 is fitted to the belly of the waistline of the wearer. The main body 10 is fitted to the crotch of the wearer.

The main body 10 in the specifically illustrated configuration has a rectangular shape. The back side flap 20 is attached to the main body 10 in an end region 10A including at least one end portion 11 in a longitudinal direction L of the main body 10. The back side flap 20 is longer than a width W in a width direction of the main body 10 (i.e., projects outwardly beyond end portions of the main body 10 in the width direction) and covers the end region 10A. The belly side flap 30 is attached to an end region 10B including at least the other end portion 12 of the main body 10. The belly side flap 30 is longer than the width W of the main body 10 and covers the end region 10B. Gathers 13, 14 are formed in end regions 10C, 10D in the width direction of the main body 10, respectively.

The main body 10 and the back side flap 20 are joined to each other in joint portions 51, 52 with an adhesive such as an HMA (hot-melt adhesive). When the disposable diaper 1 is spread out, elastics (elastics 123a, 124a to be described later with respect to FIG. 3), which are the outermost among multiple elastics included in the gathers 13, 14, are positioned, in the width direction, outboard of the joint portions 51, 52, respectively. Specifically, the joint portions 51, 52 are formed, in the width direction, inboard of imaginary lines L1 along which the outermost elastics 123a, 124a extend. The main body 10 and the belly side flap 30 are joined to each other in joint portions 53, 54 with an adhesive such as an HMA. Likewise, elastics, which are the outermost among the multiple elastic members included in the gathers 13, 14, are positioned, in the width direction, outboard of the joint portions 53, 54.

This means that the main body 10 has portions which (i) are covered with the back side flap 20 or the belly side flap 30, (ii) are included respectively in regions S1, S2 outboard of the joint portions 51, 52 (joint portions 53, 54) in the width direction of the main body 10, and (iii) are not joined (free of direct attachment) to the back side flap 20 or the belly side flap 30.

The joint portions 51, 52 are continuous from one end portion 21 to the other end portion 22 of the back side flap 20 in the longitudinal direction L. The joint portions 53, 54 are continuous from one end portion 31 to the other end portion 32 of the belly side flap 30 in the longitudinal direction L.

End portions 13r, 14r of the effective length of the respective gathers 13, 14 in the longitudinal direction overlap the back side flap 20 in a plan view of the disposable diaper 1. Likewise, the other end portions 13f, 14f of the effective length of the respective gathers 13, 14 overlap the belly side flap 30 in the plan view of the disposable diaper 1. Specifically, the effective length of the gathers 13, 14 is a length of the elastics 123, 124 which are fixed to a sheet in a stretched state to form the gathers 13, 14, respectively. In a specific configuration of this embodiment, the effective length is the length of the elastics 123a, 124a and elastics 123b, 124b. In addition, the end portions of the effective length are end portions of each of the elastics 123a, 123b, 124a, 124b.

In some exemplary configurations, the overlapping portions between the end portions 13r, 14r and the back side flap 20 have a length from 5 mm to 30 mm in the longitudinal direction L. The overlapping portions between the end portions 13f, 14f and the belly side flap 30 have a length from 5 mm to 30 mm in the longitudinal direction L.

The back side flap 20 and the belly side flap 30 are each formed of a hydrophobic nonwoven fabric, moisture-permeable or moisture-impermeable film, or a conjugated sheet obtained by bonding the hydrophobic nonwoven fabric and the moisture-permeable or moisture-impermeable film. Exemplary materials include: a film mainly made of polyethylene, polypropylene or the like; a permeable resin film; and a sheet obtained by bonding a permeable resin film to a nonwoven fabric such as a spunbond nonwoven fabric or a spunlace nonwoven fabric.

As an example, the back side flap 20 and the belly side flap 30 are formed of an SMS nonwoven fabric (a conjugated nonwoven fabric formed of a melt-blown fabric sandwiched between two layers of spun-bond nonwoven fabric) having a mass per unit area of 13 g/m$^2$, and the back side flap 20 has two layers of the SMS nonwoven fabric at least at free ends 20A, 20B in the width direction.

Fastening tapes 41, 42 are joined to the back side flap 20. Specifically, the fastening tapes 41, 42 are attached to the back side flap 20 on the free ends 20A, 20B, respectively. The fastening tapes 41, 42 are releasably fastened to the end region 10B on the other side in the longitudinal direction L of the main body 10. A fastening portion 43 to which the fastening tapes 41, 42 are releasably fastened is provided on the garment facing side of the end region 10B. The fastening tapes 41, 42 are each a male member of a so-called hook-and-loop fastener, while the fastening portion 43 is a female member. The reversed arrangement is within the scope of this disclosure.

A fastening surface having multiple hook-shaped protrusions (also referred to herein as "hooks") are formed on the fastening tapes 41, 42. An example of a material of the fastening tapes 41, 42 includes a polypropylene spunbond nonwoven fabric (PPSB). In some embodiments, it is preferable to use a PPSB having a mass per unit area of at least 80 g/m$^2$. The mass per unit area of the hooks is preferably 100 g/m$^2$ in some embodiments.

The fastening portion 43 to which the fastening tapes 41, 42 are releasably fastened is a nonwoven or woven or knitted fabric capable of releasably engaging the hooks. Conjugated fiber having a sheath-core structure is used as a fibrous material forming the nonwoven fabric in some exemplary configurations. The fibrous material uses a combination of core and sheath components, for example, polypropylene (PP)/polyethylene (PE), PP/low melting PP, polyethylene terephthalate (PET)/low melting PET, or PET/PE. The fibrous material in some embodiments is mixed with fiber such as rayon, PET, PP, polyamide such as nylon, acryl, urethane, cotton or the like. For example, the mass per unit area of the female member is 38 g/m$^2$.

Figure 3:
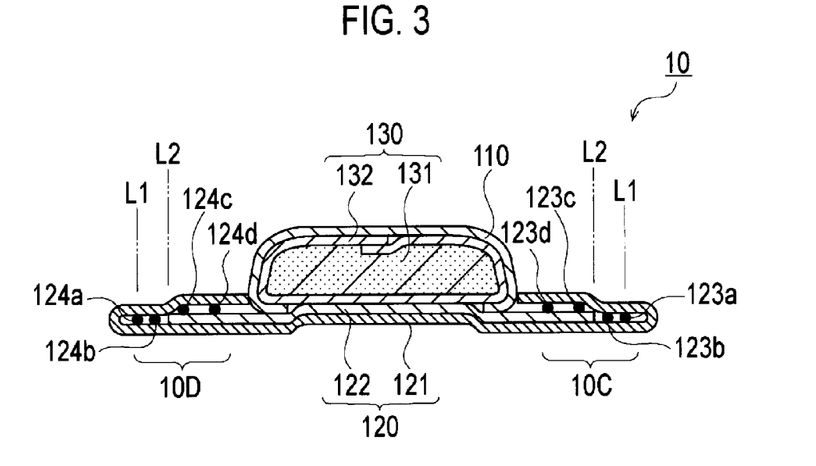
FIG. 3 is a cross-sectional view taken along the A-A' line in FIG. 1.
Figure 4:
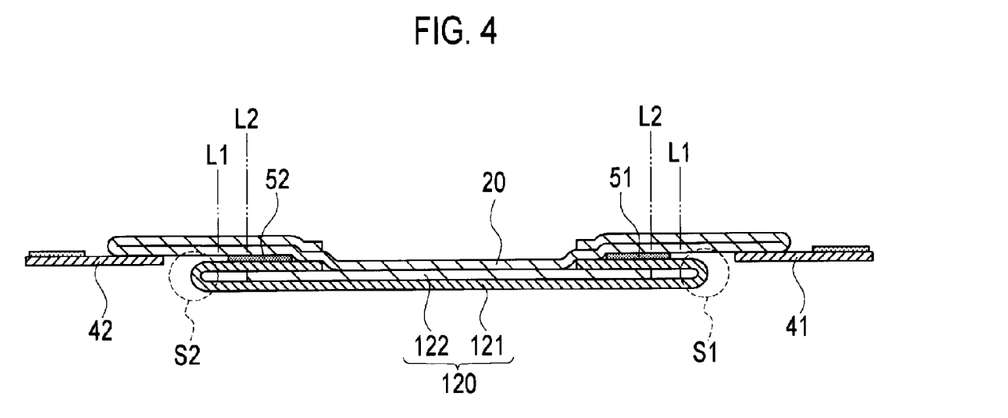
FIG. 4 is a cross-sectional view taken along the B-B' line in FIG. 1.

Next, a configuration of the main body 10 will be described. FIG. 3 is a cross-sectional view taken along the A-A' line. FIG. 4 is a cross-sectional view taken along the B-B' line.

The main body 10 includes: a liquid-permeable topsheet 110 arranged on the skin facing side; an outer sheet 120 arranged on the garment facing side; and an absorber 130.

The topsheet 110 is not particularly limited, as long as it is a sheet material having a liquid-permeable structure, such as a nonwoven fabric, a woven fabric, a porous plastic sheet, a mesh sheet, or the like. Any natural fiber and/or chemical fiber is/are usable as a material of the woven fabric and/or the nonwoven fabric.

Examples of the natural fiber as the material for the topsheet 110 include cellulose such as comminuted wood pulp or cotton. In addition, examples of the chemical fiber as the material for the topsheet 110 include regenerated cellulose, such as rayon and fibril rayon, semisynthetic cellulose, such as acetate and triacetate, thermoplastic hydrophobic chemical fiber, and hydrophilically-treated thermoplastic hydrophobic chemical fiber. Moreover, examples of the thermoplastic hydrophobic chemical fiber include single fiber such as polyethylene (PE), polypropylene (PP), polyethylene terephthalate (PET), graft-polymerized fiber of PE and PP, and compound fiber of a sheath-core structure or the like. For example, the topsheet 110 is an air-through nonwoven fabric having a mass per unit area of 18 g/m$^2$.

Methods of forming a nonwoven fabric include, either a dry method (a carding method, a spunbond method, a melt-blown method, an air-laying method or the like) or a wet method or any combinations of multiple such dry and/or wet methods. Examples of further methods include thermal bonding, needle punching, chemical bonding and the like. The method of forming the nonwoven fabric is not limited to the above methods.

The outer sheet 120 includes a back nonwoven fabric 121 on the garment facing side and a liquid-impermeable film (hereinafter, referred to as a back film) 122 on the skin facing side and adapted to be located closer to the wearer's skin than the back nonwoven fabric 121. The back film 122 is formed of a moisture-permeable or moisture-impermeable film. The back nonwoven fabric 121 is a hydrophobic nonwoven fabric, which is formed of an SMS, a spunbond or a point-bond nonwoven fabric. The back nonwoven fabric 121 and the back film 122 are bonded to each other with an HMA or the like. For example, the back film 122 is an impermeable film having a mass per unit area of 20 g/m$^2$, while the back nonwoven fabric 121 is an SMS nonwoven fabric having a mass per unit area of 13 g/m$^2$.

As best seen in FIG. 4, at first positions outboard of end portions of the back film 122 in the width direction, the back nonwoven fabric 121 is folded back onto the upper side (the skin facing side) of the back film 122. The material forming the back side flap 20 is also folded at second positions further outboard of the first positions in the width direction, so that the free ends 20A, 20B are formed. The fastening tapes 41, 42 are attached to the free ends 20A, 20B.

Multiple long and narrow (elongated) elastics, which are the elastics 123a, 123b, 124a, 124b and elastics 123c, 123d, 124c, 124d, are arranged in and fixed to end regions 10C, 10D in the width direction of the main body 10, on the skin facing side surface of the back film 122, while being stretched along the longitudinal direction L of the main body 10. The end regions of the back nonwoven fabric 121 in the width direction are folded back onto the elastics, so that the gathers 13, 14 are formed.

In a specific configuration of this embodiment, the elastics 123a, 124a are arranged outboard of the joint portions 51, 52, 53, 54 joining the belly side flap 30 and the main body 10 in the width direction of the main body 10. For example, the outer elastics 123a, 123b, 123c, 124a, 124b, 124c arranged outward in the width direction of the main body 10 have a diameter of 670 dtex, and are fixed to the main body 10 while being stretched 2.5 times. Meanwhile, the inner elastics 123d, 124d arranged inward in the width direction of the main body 10 have a diameter of 470 dtex, and are fixed to the main body 10 while being stretched 2.3 times.

The absorber 130 includes an absorbent core 131 which absorbs liquid and an absorbent sheet 132. The absorbent core 131 includes hydrophilic fiber and a super absorbent polymer. Examples of the hydrophilic fiber include cellulose, such as comminuted wood pulp and cotton, regenerated cellulose, such as rayon and fibril rayon, semisynthetic cellulose, such as acetate and triacetate, a particulate polymer, a fibrous polymer, thermoplastic hydrophobic chemical fiber, hydrophilically-treated thermoplastic hydrophobic chemical fiber or the like, or any mixture thereof. Among these materials, it is preferable in some embodiments to use the comminuted wood pulp in consideration of the cost and ease of absorbent molding.

The absorbent core 131 is wrapped with the absorbent sheet 132. In a specific configuration of this embodiment, the absorbent sheet 132 is a tissue. For example, a tissue having a mass per unit area of 15 g/m$^2$ may be used. The absorber 130 is bonded onto the skin facing side surface of the back film 122 with an HMA or the like while being wrapped with the topsheet 110.

The dimensions in the longitudinal direction of the absorbent core 131, the absorbent sheet 132 and the topsheet 110 are preferably equivalent to each other in some embodiments. The main body 10 and the back side flap 20 in some embodiments are bonded to each other with an adhesive such as an HMA in an entire region between the joint portions 51, 52, except a region corresponding to the absorber 130. The same applies to the joint portions 53, 54. An increase in the area of the bonded portions extending in the width direction of the main body 10 enhances the tensile strength in the engagement of the back side flap 20 and the belly side flap 30 along the waistline of the wearer.

Figure 5:
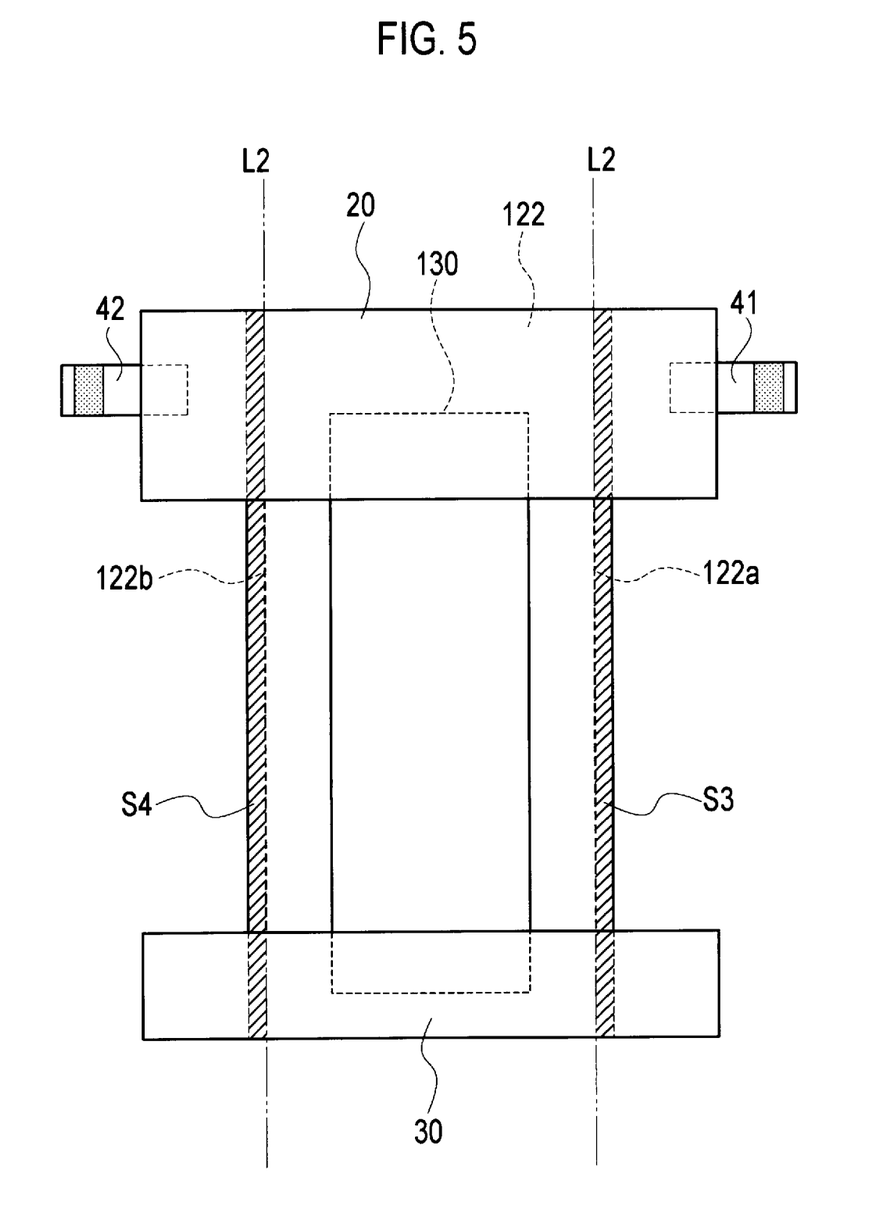
FIG. 5 is a plan view of the disposable diaper for explaining where a back film is arranged in a main body.

FIG. 5 is a view explaining where the back film 122 is arranged in the main body 10. The back film 122 is narrower in width than the back nonwoven fabric 121 even when the end portions of the back nonwoven fabric 121 in the width direction have been folded back onto the skin facing side of the back film 122. In other words, the area of the back film 122 is smaller than the area of the main body 10. Imaginary lines L2 show respective positions of end portions 122a, 122b of the back film 122 in the width direction. In the main body 10, regions S3, S4 outboard of the imaginary lines L2 are formed by only the back nonwoven fabric 121 thus folded back, i.e., free of the back film 122.

In a specific configuration of this embodiment, the imaginary lines L2 are located inboard of the imaginary lines L1 in the width direction of the main body 10 as best seen in FIGS. 3 and 4.

Figure 6:
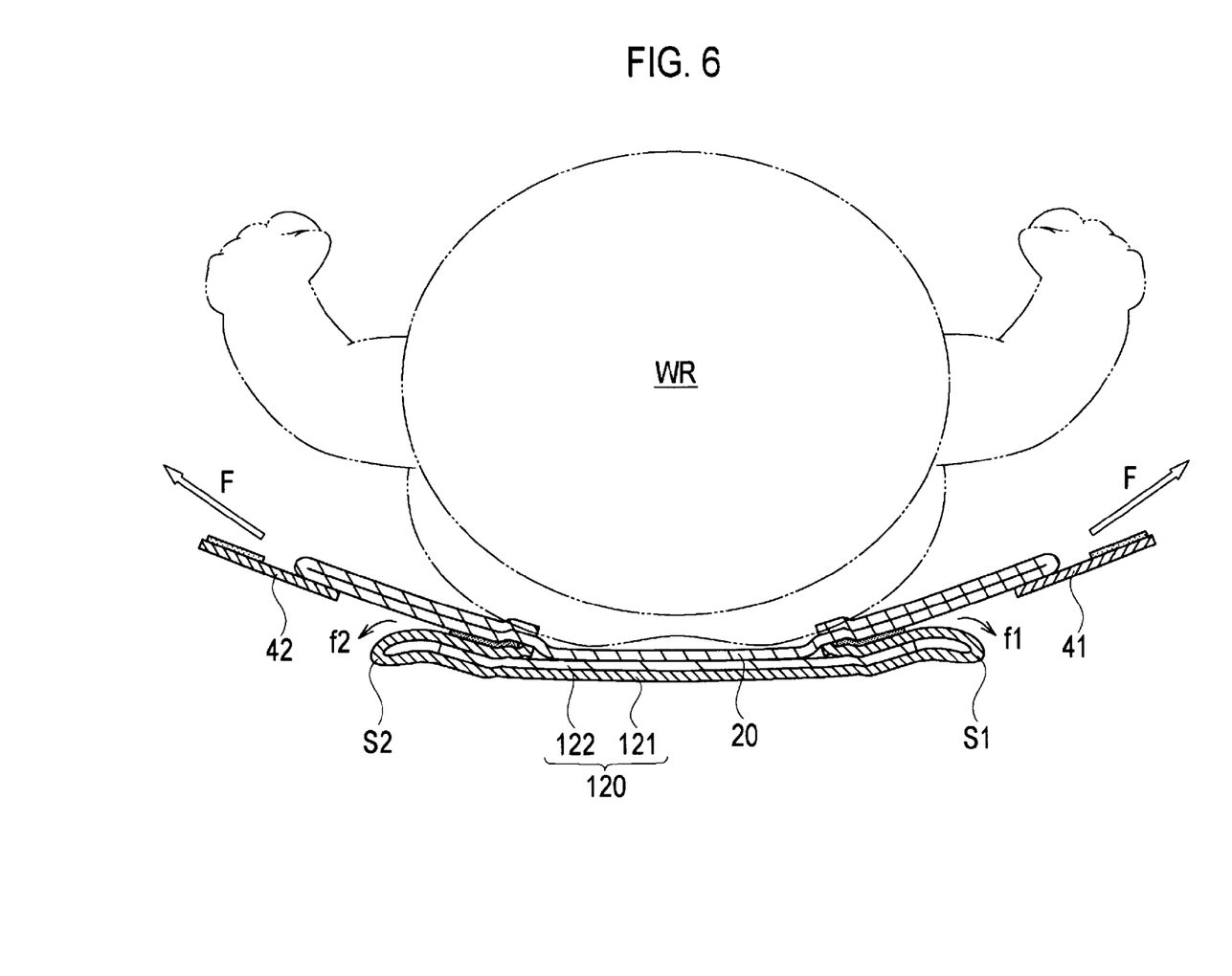
FIG. 6 is a view similar to FIG. 4 for explaining a state in which back side flaps of the disposable diaper are spread.
Figure 7:
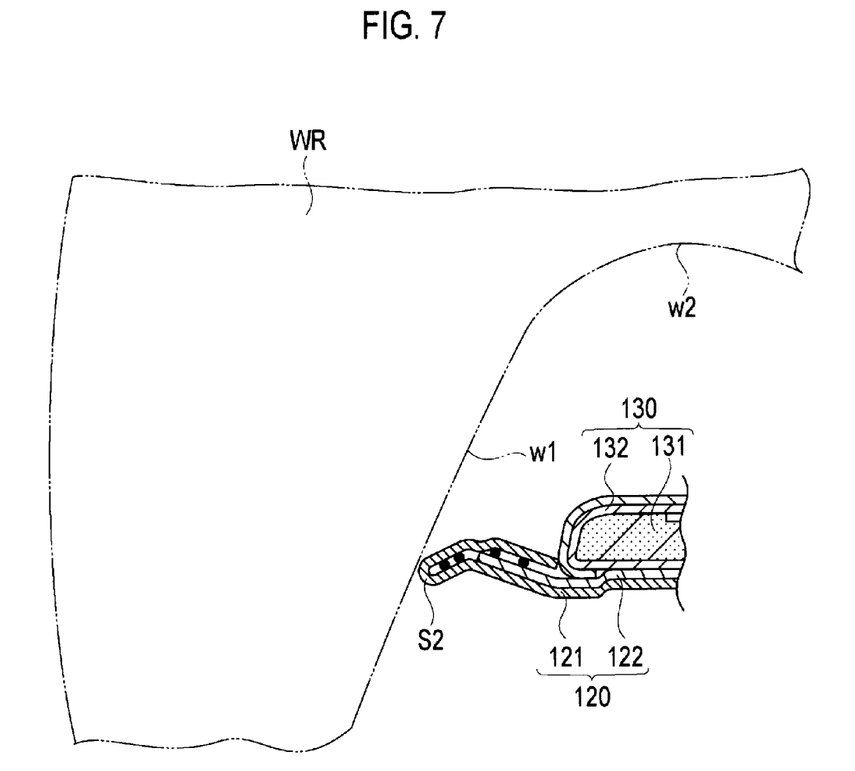
FIG. 7 is a view similar to a part of FIG. 3 for explaining a state in which the back side flaps of the disposable diaper are spread.

FIG. 6 is a view similar to FIG. 4 for explaining a state of the disposable diaper 1 with the back side flap 20 extended along the waist line of a wearer WR when the disposable diaper 1 is being put on the wearer WR. FIG. 6 shows the wearer WR represented by an imaginary line and the cross section of the disposable diaper 1 taken along the B-B' line. FIG. 7 is a view similar to a part of FIG. 3 for explaining a state of the gathers 13, 14 (only the left side is shown in FIG. 7) of the disposable diaper 1 when the disposable diaper 1 is being put on the wearer WR, and shows the cross section of the disposable diaper 1 taken along the A-A' line.

In the disposable diaper 1, since the main body 10 is not bonded onto the back side flap 20 and the belly side flap 30 in the regions S1, S2 outboard of the joint portions 51, 52 in the width direction, the main body 10 is less likely to be influenced by the movement of the back side flap 20 and the belly side flap 30 in the regions S1, S2.

Accordingly, when the back side flap 20 and the main body 10 are stretched in a direction of an arrow F in FIG. 6, forces are generated from the joint portions 51, 52 as origins, following the stretching motion. Consequently, the main body 10 is likely to warp in the regions S1, S2, which are not bonded to the back side flap 20, in directions (directions of arrows f1, f2) away from the wearer.

When the main body 10 warps in the regions S1, S2 in the directions of the arrows f1, f2, respectively, a crotch portion of the main body 10 is extended outward in the width direction, in the regions S1, S2 (only S2 is shown in FIG. 7) located in end portions of the gathers 13, 14 which are arranged correspondingly to the crotch of the wearer WR. When the belly side flap 30 (not shown in FIG. 7) is pulled toward the belly of the wearer WR in this state, the absorber 130 is fitted to the crotch w2 of the wearer WR, while the regions S1, S2 extending outward in the width direction come in contact with thighs w1 of the wearer WR. Thus, it is possible to prevent the disposable diaper 1 from being put on the wearer with the gathers 13, 14 covering part of the absorbent surface of the absorber 130.

Figure 8:
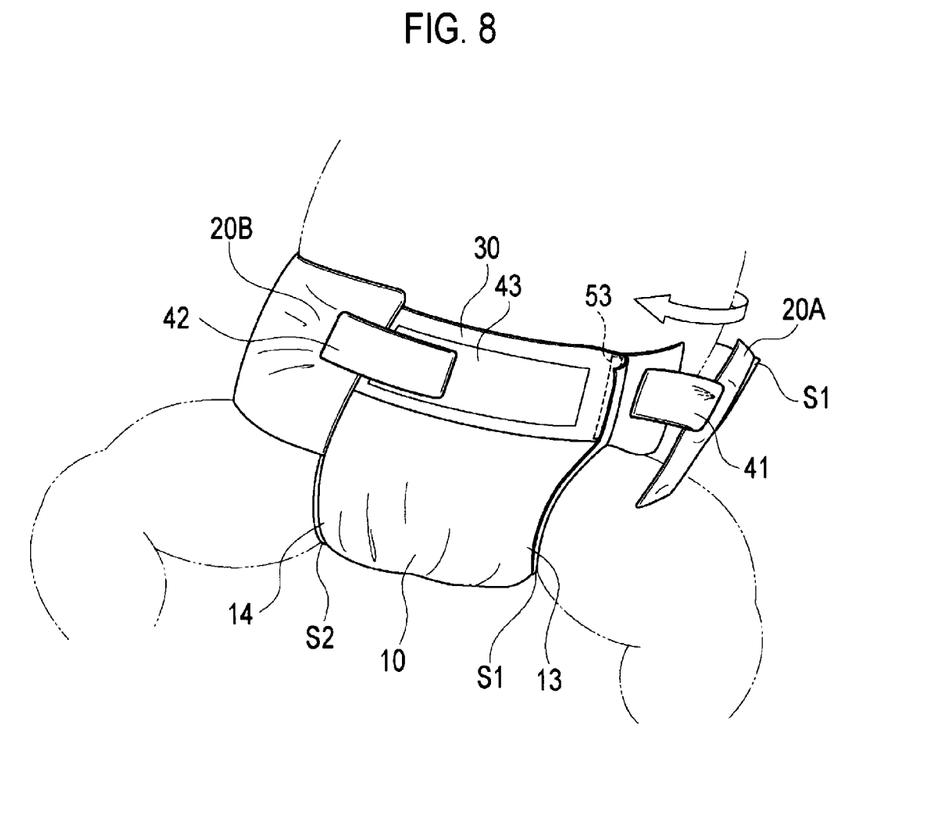
FIG. 8 is a perspective view of the disposable diaper as being worn by a wearer.

FIG. 8 is a perspective view of the disposable diaper 1 as being put halfway on the wearer WR. As discussed above with respect to the back side flap 20, when (in a state shown in FIG. 8) the belly side flap 30 is fitted to the belly of the wearer WR, the main body 10 is likely to warp in the directions away from the wearer in the regions S1, S2 (only S1 is shown in FIG. 8) which are not bonded to the belly side flap 30 at the joint portions 53, 54.

In this way, the disposable diaper 1 is prevented from being put on the wearer with the gathers 13, 14 covering part of the absorbent surface. Thus, it is possible to appropriately fit the gathers 13, 14 to the thighs of the wearer and to thereby prevent excrement from leaking through gaps between the gathers 13, 14 and the skin surfaces (the peripheries of the thighs).

Since the main body 10 in the regions S3, S4 outboard of the end portions (the imaginary lines L2) of the back film 122 is formed of only the back nonwoven fabric 121, the main body 10 in the regions S3, S4 is thinner than in the other portions of the main body 10. For this reason, the disposable diaper 1 has a smaller stiffness in the regions S3, S4 than in the portion including the back film 122 (inboard of the imaginary lines L2), and thus the back nonwoven fabric 121 is likely to be bent about the imaginary lines L2. In addition, having less layers of material in the regions S3, S4 than in the other regions, the disposable diaper 1 has enhanced air permeability.

The regions S3, S4 formed by folding only the back nonwoven fabric 121 include the elastics 123a, 123b, 124a, 124b as best seen in FIG. 3. The presence of less layers of material in the regions S3, S4 than in the other regions helps the regions S3, S4 follow the stretching and contracting of the elastics 123a, 123b, 124a, 124b. In particular, since the regions S3, S4 are brought into contact with the groin of the wearer, the fitness of the disposable diaper 1 is enhanced.

Method of Manufacturing Disposable Diapers

Figure 9:
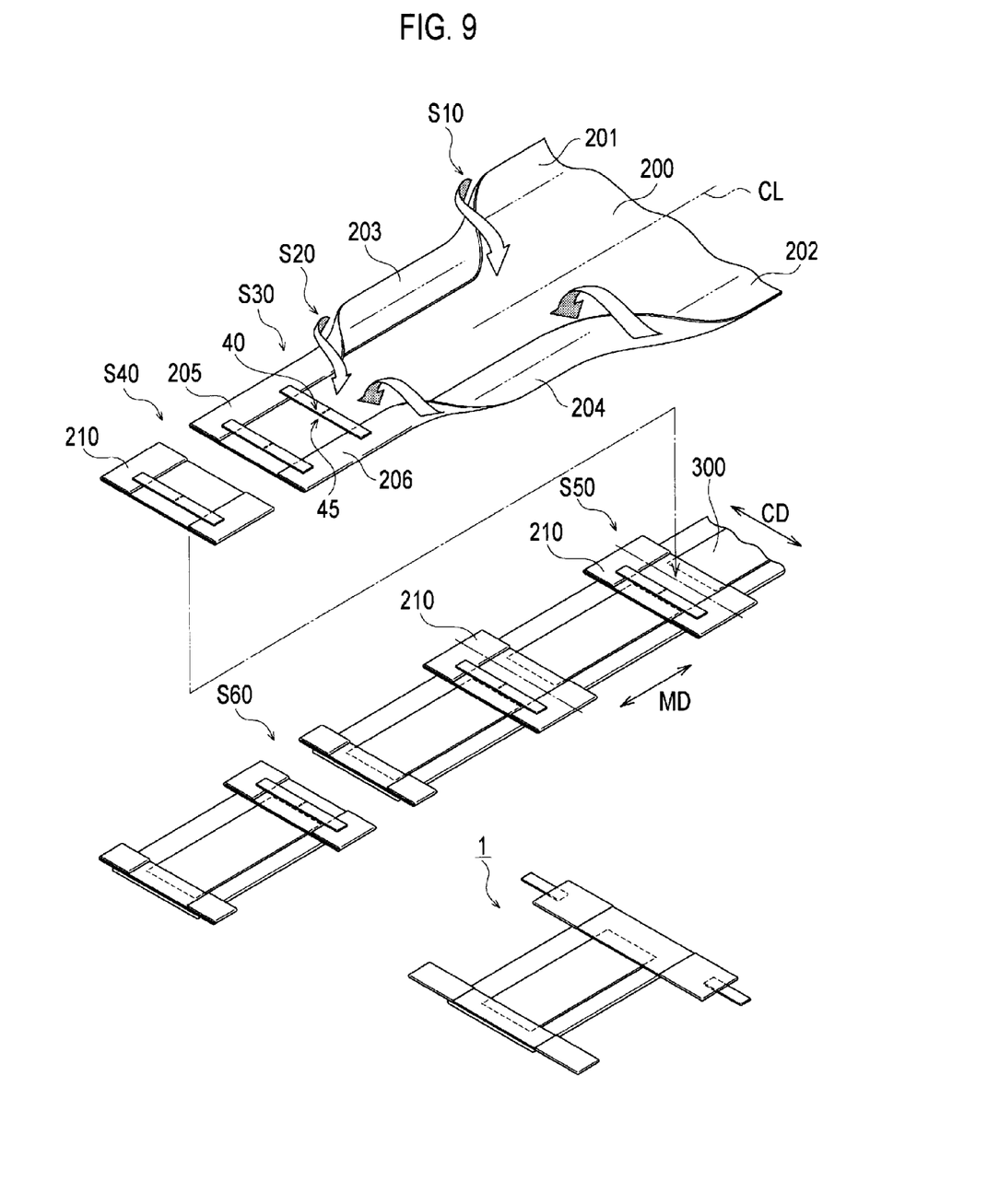
FIG. 9 is a view of various stages during a manufacturing process of the disposable diaper according to an embodiment of the present invention.

Next, a method of manufacturing the disposable diaper 1 will be described with reference to FIG. 9. As shown in FIG. 9, the method includes a first folding step S10, a second folding step S20, a fastening-tape attaching step S30, a first cutting step S40, a flap attaching step S50, and a second cutting step S60.

In the first folding step S10, end portions 201, 202 of a flap sheet 200 which is continuous in a conveyance direction (machine direction) MD are folded back toward a center line CL onto the upper surface of the flap sheet 200, and the folded end portions 201 and 202 are bonded to the upper surface of the flap sheet 200 with an HMA, by embossing or the like. The center line CL is located in the center in the width direction (or a cross direction CD which is orthogonal to the conveyance direction MD) of the flap sheet 200.

In the second folding step S20, folded end portions 203, 204 obtained after the first folding step S10 are further folded toward the center line CL onto the upper side of the flap sheet 200. Thereby, overlapped portions 205, 206 are formed in end portions of the flap sheet 200, the overlapped portions 205, 206 having multiple layers of the flap sheet 200. The overlapped portions 205, 206 form the free ends 20A, 20B of the back side flap 20, respectively. The overlapped portions 205, 206 thus formed in the second folding step S20 are not bonded to the flap sheet 200.

In the fastening-tape attaching step S30, the fastening tapes 41, 42 are attached to the flap sheet 200 at predetermined intervals in the conveyance direction MD. In the manufacturing process, the fastening tapes 41, 42 are an integrated member (referred to as a fastening tape 40). The fastening tape 40 is processed for easy separation in the conveyance direction MD, in the center thereof, for example, by including a perforated line 45.

In the first cutting step S40, the flap sheet 200 is cut in the cross direction CD orthogonal to the conveyance direction MD, at predetermined intervals. Each piece 210 cut from the flap sheet 200 defines one back side flap 20 and one belly side flap 30 which are integrated with each other.

In the flap attaching step S50, the pieces 210 cut from the flap sheet 200 are arranged on a main body sheet 300 at predetermined intervals. The main body sheet 300 has been produced by arranging absorbent cores intermittently on a continuous web of outer sheets. Each of the pieces 210 is arranged on the main body sheet 300 to cover a gap between the intermittently arranged absorbent cores, and is bonded onto the main body sheet 300 at predetermined positions.

In the second cutting step S60, the main body sheet 300 with the pieces 210 attached thereto are cut in the cross direction CD. Each cut piece 210 is separated into the belly side flap 30 of a diaper and the back side flap 20 of another diaper. As the result of the second cutting step S60, the disposable diaper 1 is completed.

MODIFIED EMBODIMENTS

Figure 10:
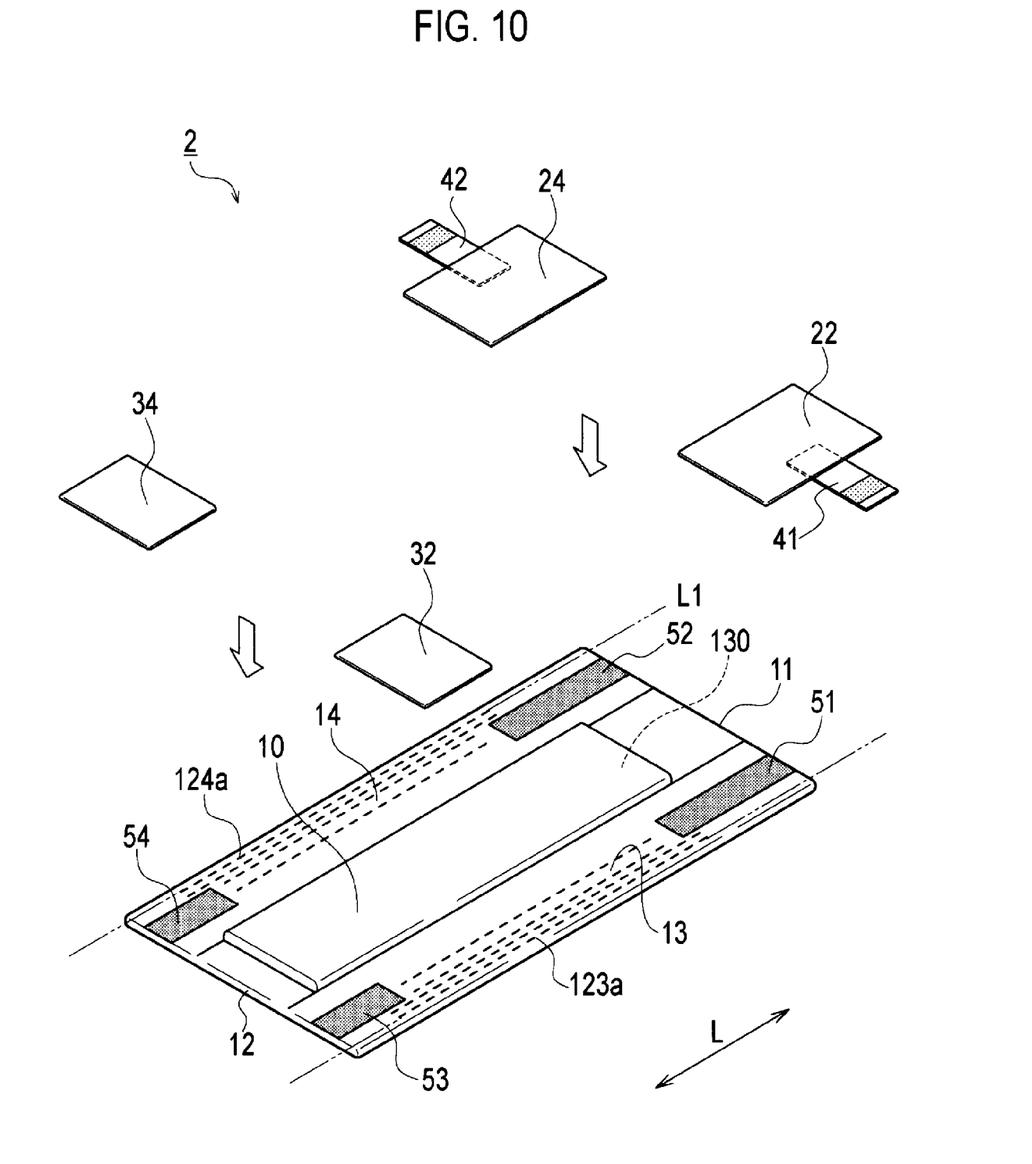
FIG. 10 is an exploded perspective view of a disposable diaper according to a modified embodiment of the present invention.

Next, a disposable diaper 2 according to a modified embodiment will be described by using FIG. 10. The disposable diaper 2 is provided with separate right and left side flaps. The end portions 10A, 10B are not completely covered with a back side flap and a belly side flap. In other words, the disposable diaper 2 includes back side flaps 22, 24, and belly side flaps 32, 34. The joint portions 51, 52, 53 and 54 join the back side flaps 22, 24, and the belly side flaps 32, 34 to the main body 10, respectively. The same effect as in the disposable diaper 1 can be obtained also in the disposable diaper 2.

OTHER EMBODIMENTS

As described above, the details of several embodiments of the present invention have been exemplarily disclosed. However, it should not be understood that the description and drawings which constitute part of this disclosure limit the present invention. From this disclosure, various alternative embodiments, examples, and operation techniques will be found by those ordinarily skilled in the art.

For examples, the description has been given for the disposable diaper 1 in which the back side flap 20 and the belly side flap 30 are attached to the main body 10. However, further embodiments are not limited thereto. For example, the disposable diaper may be a pants-type disposable diaper formed by integrally providing a waistline region for the waistline of the wearer and a crotch region for the crotch and by cutting out openings for the legs of the wearer. The disposable diaper 1 may be of any size for infants, children or adults.

Note that the entire contents of the Japanese Patent Application No. 2009-230041, filed on Oct. 1, 2009 is incorporated herein by reference.

Further, the aspects of the present invention may be arranged described in at least the following items. In the disposable diaper, the side flap may be longer in the width direction than the main body is, and covers said an end region including at least the one of the end portion of the main body in the longitudinal direction thereof, and projects outwardly beyond both the end portions of the main body in the width direction.

In the disposable diaper, the side flap partially may cover said one of the end portions of the main body in the longitudinal direction, and projects outwardly beyond only one of the end portions of the main body in the width direction; the diaper further comprising a further side flap which partially covers said one of the end portions of the main body in the longitudinal direction, and projects outwardly beyond the other one of the end portions of the main body in the width direction.

In the disposable diaper, the main body may include a region which is covered with the side flap, positioned outboard of the joint portion in the width direction, and free of direct attachment to the side flap. In the disposable diaper, said region of the main body may be configured to warp away from a waistline of a wearer when the diaper is being put on the wearer.

In the disposable diaper, the outer sheet may comprise a back nonwoven fabric arranged on a garment-facing side; and a liquid-impermeable back film which is arranged between the back nonwoven fabric and the absorber and is at least narrower than the back nonwoven fabric in the width direction, and said region of the main body is defined by the back nonwoven fabric and is free of the back film.

In the disposable diaper, the main body may include in said region a further region which is positioned outboard of the outermost elastic member in the width direction, and defined only by the back nonwoven fabric. In the disposable diaper, said further region of the main body may be configured to warp away from a wearer when the diaper is being put on the wearer.

In the disposable diaper, an effective length of the gather as defined by effective lengths of the elastic members overlaps the side flap in the longitudinal direction. In the disposable diaper, the effective length of the gather may overlap the side flap in the longitudinal direction by 5 to 30 mm.

Further, the disposal diaper may comprise: a main body having two end portions disposed in the longitudinal direction of the main body; the main body comprising: a liquid-permeable topsheet, a liquid-impermeable outer sheet, an absorber provided between the topsheet and the outer sheet, and a gathered region including a plurality of elongate elastic members arranged substantially in parallel with each other, located outwardly in a width direction of the absorber and provided in a state where the plurality of elastic members are stretched in a longitudinal direction of the absorber; wherein the diaper further comprises at least one side flap which is located at one end portion of the main body adjacent the gathered region and is continuous to the end portion of the main body in a width direction thereof; wherein a joint portion is configured to join the side flap and the main body, and wherein, in an extended state of the disposable diaper, at least one elastic member arranged outermost among the plurality of elastic members is arranged outward of the joint portion in the width direction of the main body.

In one embodiment, only one elastic member of a gathered region is arranged outward of the adjacent joint portion. Generally-speaking, a diaper will have a gathered region extending in the longitudinal direction along each of its side edges, in order to provide leakage-prevention portions.

In one embodiment, the side flap is longer than the width of the main body and is arranged such that it extends outwardly on both sides of the main body in its width direction and covers an end region including at least the one end portion of the main body in the longitudinal direction thereof.

In an alternative embodiment, two side flaps are provided at one end portion of the main body, one side flap extending outwardly in a direction along the width of the main body and the other side flap extending outwardly in an opposite direction along the width of the main body.

Preferably, at least one side flap is also located at the opposite end portion of the main body adjacent the gathered region and continuous to said opposite end portion of the main body in a width direction; wherein a joint portion is configured to join the side flap and the main body, and wherein, in an extended state of the disposable diaper, an elastic member arranged outermost among the plurality of elastic members is arranged outward of the joint portion in the width direction of the main body.

This side flap, in one embodiment, is preferably longer than the width of the main body and is arranged such that it extends outwardly on both sides of the main body in its width direction and covers an end region including at least said opposite end portion of the main body in the longitudinal direction thereof.

In an alternative embodiment, two of these side flaps are provided at said opposite end portion of the main body, one side flap extending outwardly in a direction along the width of the main body and the other side flap extending outwardly in an opposite direction along the width of the main body.

Preferably, the side flap or side flaps each have two opposing end portions extending in the width direction of the main body and the joint portion is continuous from one end portion to the other end portion of the side flap in the longitudinal direction of the main body.

In a preferred embodiment, the outer sheet comprises: a back nonwoven fabric arranged on a garment side; and a liquid-impermeable back film which is arranged between the back nonwoven fabric and the absorber and is shorter than the back nonwoven fabric in a width direction of the main body; wherein the plurality of elastic members are arranged substantially in parallel with each other in an outer region of the outer sheet in the width direction, and wherein the back nonwoven fabric located outward of an outermost elastic member is folded over said elastic members in the direction of the absorber to provide the gathered region.

Preferably, at least the outermost elastic member is located outwardly of the liquid-impermeable back film in the width direction of the main body and is in contact with the back nonwoven fabric but is not in contact with the liquid-impermeable back film.

Preferably, the surface area of the liquid-impermeable back film is smaller than the surface area of the main body as defined by the outer sheet.

In one embodiment, the folding of the back nonwoven fabric provides the outer sheet with an outer end portion along its length, said outer end portion consisting of the back nonwoven fabric and any elastic members wrapped therein. The outer end portion does not include the back film. It may include one or more elastic members along some or all of its length. In the embodiment described above, this outer end portion corresponds to one of regions S3 and S4.

Preferably, at least an outermost region of the outer end portion of the outer sheet lies outward of the joining portion such that it is unbonded to an adjacent side flap. In the embodiment described above, this outermost region of the outer end portion corresponds to one of regions S1 and S2.

The invention claimed is:
1. A disposable diaper, comprising:
a main body having a longitudinal direction and a width direction orthogonal to the longitudinal direction, said main body including
a liquid-permeable topsheet,
a liquid-impermeable outer sheet,
an absorber provided between the topsheet and the outer sheet, and
a gather including a plurality of elastic members arranged, in the width direction, outboard of the absorber, said elastic members being fixed to the gather in a state where the elastic members are stretched in the longitudinal direction;

a side flap which is located in one of end portions of the main body in the longitudinal direction and projects outwardly beyond at least one of lateral end portions of the main body in the width direction; and a joint portion joining the side flap and the main body, wherein in a spread-out state of the disposable diaper, an outermost elastic member among said elastic members is arranged outboard of the joint portion in the width direction, the outer sheet includes:
  a back nonwoven fabric arranged on a garment-facing side; and
  a liquid-impermeable back film which is arranged between the back nonwoven fabric and the absorber and is at least narrower than the back nonwoven fabric in the width direction, the outermost elastic member is arranged outboard of the back film in the width direction, the gather is defined by an end portion of the back nonwoven fabric which is located outboard of the outermost elastic member and is folded back onto an upper side of the back nonwoven fabric to cover the elastic members, the outermost elastic member overlaps the side flap in a thickness direction of the main body and in the spread-out state, the main body includes a region which is
  (i) covered with the side flap,
  (ii) positioned outboard of the joint portion in the width direction, and
  (iii) free of direct attachment to the side flap, and said region of the main body is defined by the back nonwoven fabric and is free of the back film.

2. The disposable diaper according to claim 1, wherein
the side flap is longer in the width direction than the main body, and
the side flap covers said one of the end portions of the main body in the longitudinal direction thereof.

3. The disposable diaper according to claim 1, wherein the joint portion is continuous from one end portion to the other end portion of the side flap in the longitudinal direction.

4. The disposable diaper according to claim 1, wherein the main body includes in said region a further region which is
  (i) positioned outboard of the outermost elastic member in the width direction, and
  (ii) defined only by the back nonwoven fabric.

5. The disposable diaper according to claim 4, wherein said further region of the main body is configured to warp away from a wearer when the diaper is worn on the wearer.

6. The disposable diaper according to claim 1, wherein an effective length of the gather is defined by effective lengths of the elastic members and overlaps the side flap in the longitudinal direction.

7. The disposable diaper according to claim 6, wherein the effective length of the gather overlaps the side flap in the longitudinal direction by 5 to 30 mm.

8. The disposable diaper according to claim 1, wherein the joint portion is arranged adjacent to the absorber in the width direction and does not overlap the absorber in the thickness direction of the main body.

9. A disposable diaper, comprising:
a main body having a longitudinal direction and a width direction orthogonal to the longitudinal direction, said main body including
  a liquid-permeable topsheet,
  a liquid-impermeable outer sheet,
  an absorber provided between the topsheet and the outer sheet, and
  a gather including a plurality of elastic members arranged, in the width direction, outboard of the absorber, said elastic members being fixed to the gather in a state where the elastic members are stretched in the longitudinal direction;

a side flap which is located in one of end portions of the main body in the longitudinal direction and projects outwardly beyond at least one of lateral end portions of the main body in the width direction, wherein the side flap partially covers said one of the end portions of the main body in the longitudinal direction, and projects outwardly beyond only one of the lateral end portions of the main body in the width direction;

a joint portion joining the side flap and the main body; and a further side flap which partially covers said one of the end portions of the main body in the longitudinal direction, and projects outwardly beyond the other one of the lateral end portions of the main body in the width direction, wherein in a spread-out state of the disposable diaper, an outermost elastic member among said elastic members is arranged outboard of the joint portion in the width direction, the outer sheet includes:
  a back nonwoven fabric arranged on a garment-facing side; and
  a liquid-impermeable back film which is arranged between the back nonwoven fabric and the absorber and is at least narrower than the back nonwoven fabric in the width direction, the outermost elastic member is arranged outboard of the back film in the width direction, the gather is defined by an end portion of the back nonwoven fabric which is located outboard of the outermost elastic member and is folded back onto an upper side of the back nonwoven fabric to cover the elastic members, and the outermost elastic member overlaps the side flap in a thickness direction of the main body and in the spread-out state.

10. The disposable diaper according to claim 9, wherein
the side flap is longer in the width direction than the main body, and
the side flap covers said one of the end portions of the main body in the longitudinal direction thereof.

11. The disposable diaper according to claim 9, wherein the joint portion is continuous from one end portion to the other end portion of the side flap in the longitudinal direction.

12. The disposable diaper according to claim 9, wherein an effective length of the gather is defined by effective lengths of the elastic members and overlaps the side flap in the longitudinal direction.

13. The disposable diaper according to claim 12, wherein the effective length of the gather overlaps the side flap in the longitudinal direction by 5 to 30 mm.

14. The disposable diaper according to claim 9, wherein the joint portion is arranged adjacent to the absorber in the width direction and does not overlap the absorber in the thickness direction of the main body.

15. A disposable diaper, comprising:
a main body having a longitudinal direction and a width direction orthogonal to the longitudinal direction, said main body including
  a liquid-permeable topsheet,
  a liquid-impermeable outer sheet, an absorber provided between the topsheet and the outer sheet, and a gather including a plurality of elastic members arranged, in the width direction, outboard of the absorber, said elastic members being fixed to the gather in a state where the elastic members are stretched in the longitudinal direction;

a side flap which is located in one of end portions of the main body in the longitudinal direction and projects outwardly beyond at least one of lateral end portions of the main body in the width direction; and a joint portion joining the side flap and the main body, wherein in a spread-out state of the disposable diaper, an outermost elastic member among said elastic members is arranged outboard of the joint portion in the width direction, the outer sheet includes:
- a back nonwoven fabric arranged on a garment-facing side; and
- a liquid-impermeable back film which is arranged between the back nonwoven fabric and the absorber and is at least narrower than the back nonwoven fabric in the width direction, the outermost elastic member is arranged outboard of the back film in the width direction, the gather is defined by an end portion of the back nonwoven fabric which is located outboard of the outermost elastic member and is folded back onto an upper side of the back nonwoven fabric to cover the elastic members, the outermost elastic member overlaps the side flap in a thickness direction of the main body and in the spread-out state, the main body includes a region which is
(i) covered with the side flap,
(ii) positioned outboard of the joint portion in the width direction, and
(iii) free of direct attachment to the side flap, and said region of the main body is configured to warp away from a waistline of a wearer when the diaper is worn on the wearer.

16. The disposable diaper according to claim 15, wherein the side flap is longer in the width direction than the main body, and the side flap covers said one of the end portions of the main body in the longitudinal direction thereof.

17. The disposable diaper according to claim 15, wherein the joint portion is continuous from one end portion to the other end portion of the side flap in the longitudinal direction.

18. The disposable diaper according to claim 15, wherein an effective length of the gather is defined by effective lengths of the elastic members and overlaps the side flap in the longitudinal direction.

19. The disposable diaper according to claim 18, wherein the effective length of the gather overlaps the side flap in the longitudinal direction by 5 to 30 mm.

20. The disposable diaper according to claim 15, wherein the joint portion is arranged adjacent to the absorber in the width direction and does not overlap the absorber in the thickness direction of the main body.

* * * * *